United States Patent
Leschinski et al.

(10) Patent No.: US 8,609,887 B2
(45) Date of Patent: Dec. 17, 2013

(54) PROCESS FOR PREPARING POLYISOCYANATES COMPRISING BIURET GROUPS

(75) Inventors: Julia Leschinski, Ixelles (BE); Torsten Mattke, Freinsheim (DE); Gerrit Waters, Karlsruhe (DE); Horst Binder, Lampertheim (DE); Harald Schaefer, Mannheim (DE); Matthias Kroner, Eisenberg (DE); Alexander Bayer, Limburgerhof (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/409,657

(22) Filed: Mar. 1, 2012

(65) Prior Publication Data
US 2012/0226071 A1 Sep. 6, 2012

Related U.S. Application Data

(60) Provisional application No. 61/448,679, filed on Mar. 3, 2011.

(51) Int. Cl.
*C07C 263/00* (2006.01)

(52) U.S. Cl.
USPC .......................................................... 560/347

(58) Field of Classification Search
None
See application file for complete search history.

(56) References Cited

U.S. PATENT DOCUMENTS

| | | | |
|---|---|---|---|
| 4,596,678 A | 6/1986 | Merger et al. | |
| 4,596,679 A | 6/1986 | Hellbach et al. | |
| 5,087,739 A | 2/1992 | Bohmholdt et al. | |
| 6,414,184 B1 * | 7/2002 | Bruchmann et al. | 560/335 |

FOREIGN PATENT DOCUMENTS

| | | |
|---|---|---|
| DE | 2 005 309 | 8/1970 |
| DE | 1 931 055 | 12/1970 |
| DE | 2 261 065 | 6/1974 |
| DE | 24 04 773 | 8/1975 |
| DE | 26 09 995 | 9/1977 |
| DE | 44 43 885 A1 | 6/1996 |
| DE | 196 33 404 A1 | 2/1998 |
| DE | 197 07 576 C1 | 4/1998 |
| DE | 10 2004 060 739 A1 | 6/2006 |
| EP | 0 003 505 A1 | 8/1979 |
| EP | 0 012 973 A1 | 7/1980 |
| EP | 0 126 299 B1 | 4/1987 |
| EP | 0 126 300 B1 | 4/1987 |
| EP | 0 259 233 A2 | 3/1988 |
| EP | 0 277 353 A1 | 8/1988 |
| EP | 0 355 443 A2 | 2/1990 |
| EP | 0 568 782 A2 | 11/1993 |
| EP | 0 918 809 B1 | 11/2001 |
| EP | 1 158 013 A1 | 11/2001 |
| EP | 1 716 080 B1 | 2/2011 |
| WO | WO 96/25444 | 8/1996 |
| WO | WO 2008/110492 A1 | 9/2008 |

OTHER PUBLICATIONS

"Mixing and Blending" in Kirk-Othmer Encyclopedia of Chemical Technology, David S. Dickey, Published Online : Apr. 16, 2010, Copyright © 2001 by John Wiley & Sons, Inc., pp. 1-71.*
U.S. Appl. No. 13/660,253, filed Oct. 25, 2012, Schaefer, et al.
U.S. Appl. No. 13/479,961, filed May 24, 2012, Stroefer, et al.

* cited by examiner

*Primary Examiner* — Karl J Puttlitz
(74) *Attorney, Agent, or Firm* — Oblon, Spivak, McClelland, Maier & Neustadt, L.L.P.

(57) ABSTRACT

The present invention relates to a process for preparing polyisocyanates comprising biuret groups from diisocyanates or polyisocyanates and diamines.

14 Claims, 3 Drawing Sheets

PROCESS FOR PREPARING POLYISOCYANATES COMPRISING BIURET GROUPS

The present invention relates to a process for preparing polyisocyanates comprising biuret groups from diisocyanates or polyisocyanates and diamines.

DE 196 33 404 describes the preparation of polyisocyanates comprising biuret groups using a mixing element having a high shearing action. The application mentions the use of acid catalysts in the simultaneous presence of water or tert-butanol.

Disadvantages of the addition of water or water-releasing agents are the degradation of isocyanate groups to amine groups, since the isocyanates are prepared industrially from the corresponding amines. A further disadvantage is the formation of reaction gases, in particular carbon dioxide and isobutene, during the reaction, which leads to a gaseous/liquid reaction mixture and an exhaust gas stream. The examples without water which were explicitly carried out were all carried out at a high temperature and lead to light-colored products. Isobutene or rather the offgas stream also have to be incinerated in a plant provided industrially for this purpose.

Water or tert-butanol and other compounds which release water under the reaction conditions of the biuretization will hereinafter be referred to as biuretizing agents.

EP-A1716 080 likewise describes a process for preparing isocyanates comprising biuret groups from isocyanates and water or water vapor, with the water being introduced in finely divided form to control the reaction.

DE 10 2004 060739 describes a process for preparing polyisocyanates comprising biuret groups with addition of, for example, water as biuretizing agent under the action of high shear. This process displays the usual disadvantages of biuretization by means of a biuretizing agent.

As an alternative to the processes described hitherto with addition of biuretizing agents, the preparation of biuret-based polyisocyanates by reaction of diisocyanates and diamine has also been examined. The first advantage of this process over the reaction of diisocyanate with biuretizing agents is that neither isobutene (from tert-butanol) nor carbon dioxide are formed as undesirable by-products.

The second advantage is that theoretically about one sixth of the diisocyanate starting material is replaced by the starting material diamine which is cheaper than the diisocyanate. The diisocyanate is usually prepared from the diamine by costly phosgenation or via a phosgene-free route. Processes using diisocyanates and diamines are thus desirable compared to the reaction with water, since conversion of the diamine into the isocyanate can be dispensed with for a part of the starting material.

A disadvantage is firstly that the mixing of diamine and diisocyanate generally forms suspended solids which are not dissolved or only sparingly dissolved or can react further to form the polyisocyanate comprising biuret groups during the course of the further reaction.

DE 22 61 065 describes a process for preparing polyisocyanates comprising biuret groups from diisocyanate and amine. A disadvantage is the long residence times of the reaction mixture (see example 16 of the patent application) which are uneconomical and lead to unacceptable discoloration of the product. This process also leads to insoluble gel-like secondary components (see DE 26 09 995, page 4).

DE 2 609 995 describes a process for preparing polyisocyanates comprising biuret groups by passing gaseous diamines into diisocyanates at temperatures of from 100 to 250° C. Disadvantages are the thermal stress during vaporization of the diamines or the extra outlay when using reduced pressure. A disadvantage of the participation of gases is the mass transfer limitation between gas phase and liquid phase, which has an adverse effect on the space-time yield. After this process, a heat treatment at 120-195° C., preferably 160-180° C., for from 6 to 10 hours is necessary to improve the color, as a result of which the space-time yield is reduced.

EP 3 505 describes the preparation of biurets from diisocyanates and diamine in a flat jet nozzle mixing device in which the starting materials are mixed with high mixing power. A disadvantage of the process is the use of high reaction temperatures up to 250° C. In addition, a special apparatus is necessary (flat jet nozzle). Particularly in the case of hexamethylene 1,6-diisocyanate, higher oligomers and by-products are formed and these lead to an increase in the viscosity, an undesirable reduction in the NCO content and a reduced ability to be diluted with nonpolar solvents (cf. EP 277353, page 2).

EP 12 973 describes a process for preparing polyisocyanates comprising biuret groups using strong acids which form mixed carbamic anhydrides with isocyanates. A disadvantage is the long residence times of the reaction mixture to obtain a clear liquid comprising biuret groups, which lead to unacceptable discoloration of the product.

EP 277 353 describes a process for preparing polyisocyanates comprising biuret groups, in which the reactants are reacted at temperatures above 250° C. They still display a slightly reduced monomer stability and reduced dilution stability (cf. EP 1 158 013, page 2).

EP 1 158 013 describes the preparation of biurets from diisocyanates and diamines at temperatures above 170° C. in the presence of an acidic substance as catalyst. The examples describe mixing of the components in a mixing chamber which is not specified more precisely with rapid heating of the starting materials. A disadvantage of this process is, as in the case of EP 277 353, the higher color number compared to products which are prepared by processes using biuretizing agents.

DE-C1 197 07 576 describes a process for preparing aromatic polyisocyanates comprising biuret groups from isocyanates and diamines, in which diamine and isocyanate are reacted with one another in a single mixing chamber and are subsequently reacted to completion in a single-stage stirred vessel or optionally a multistage cascade of stirred vessels.

EP 918809 (=U.S. Pat. No. 6,414,184) describes the preparation of biurets from isocyanates and the corresponding amines or water or water-releasing agents, in which the reactants are brought into contact with one and another under the action of high shear in a mixing element. Mention is made of rotor-stator elements, Ultra-Turrax, high-speed mixers and shear disk mixers. The mode of action (by means of centrifical forces) of a rotating fixed-bed reactor differs significantly therefrom in the absence of a stator in the region of the mixture.

WO 2008/110492 describes a process for preparing polyisocyanates comprising biuret groups, in which diamine and diisocyanate are mixed with one another using a minimum mixing work in a mixing device. As mixing devices, mention is made of various mixing devices, and mixing of the components in a mixing pump is explicitly disclosed.

However, there is no concrete teaching as to what technical apparatuses can be used for such mixing.

It was an object of the present invention to provide technical apparatuses for preparing biurets from isocyanates and diamines, in which products having a reduced color compared to those obtained under comparable reaction conditions from processes of the prior art comprising the preparation of biurets without biuretizing agents, with the storage stability according to the prior art being at least retained.

The object is achieved by a process for preparing polyisocyanates comprising biuret groups from a) at least one (cyclo)aliphatic diisocyanate and/or polyisocyanate, b) at least one (cyclo)aliphatic diamine having two primary and/or secondary amino groups, c) optionally at least one acid and d) optionally at least one solvent, e) optionally in the presence of water or at least one water-releasing compound, which comprises i) mixing the components a), b) and optionally c) and also optionally d) and/or e) in a mixing device and ii) feeding the reaction mixture obtained from i) into at least one reaction apparatus in which the reaction mixture is treated thermally, where the mixing device is at least one rotating fixed-bed reactor having an acceleration acting on the liquid phase in the mixing device of at least 100 g. Here "g" is the acceleration due to gravity having a value of 9.81 m/s$^2$.

The advantage of the present invention is that polyisocyanates comprising biuret groups which have a low color number can be obtained with higher selectivity and with fewer problems involving solids formation by means of the process of the invention than when using the processes known from the prior art.

The packaging of a rotating fixed bed reactor is an additional reaction zone which other mixers such as rotor-stator elements, Ultra-Turrax, high-speed mixers and shear disk mixers do not have. Multiple mixing on various packing elements occurs. The residence time in the high shear zone is significantly longer in a rotating fixed-bed reactor than in other mixing devices.

Mixing in the rotating fixed-bed reactor results in formation of fewer and finer agglomerates than in alternative processes. Solids formation can be minimized by good mixing.

A further advantage of the present invention is therefore that clear products having good or improved storage stability when diluted with solvents (e.g. 40% strength based on biuret and below) can be obtained by reaction of diamine and diisocyanate by means of the rotating fixed-bed reactor.

Figure 1:
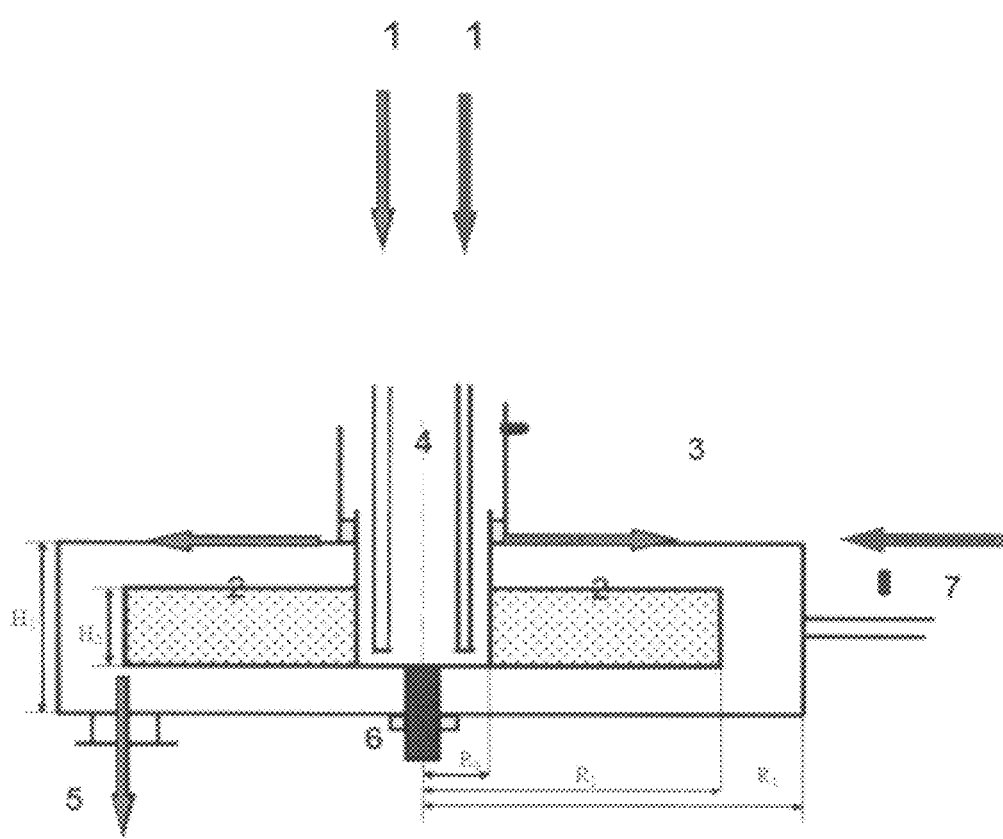
FIG. 1 shows an illustrative schematic embodiment of a rotating fixed-bed reactor as can be used for the present invention.

Suitable diisocyanates and polyisocyanates a) for the process of the invention are (cyclo)aliphatic isocyanates, i.e. compounds which have at least 2, preferably from 2 to 6, particularly preferably from 2 to 4, very particularly preferably 2 or 3 and in particular precisely 2, isocyanate groups bound to carbon atoms which are part of an aliphatic and/or cycloaliphatic system.

Suitable diisocyanates are preferably diisocyanates having from 4 to 20 carbon atoms.

Cycloaliphatic isocyanates are ones comprising at least one cycloaliphatic ring system.

Aliphatic isocyanates are ones which comprise exclusively straight or branched chains, i.e. acyclic compounds.

The terms "aliphatic" and "cycloaliphatic" are in the present text combined as (cyclo)aliphatic.

Particularly preferred aliphatic diisocyanates are tetramethylene diisocyanate, hexamethylene diisocyanate (1,6-diisocyanatohexane), octamethylene diisocyanate, decamethylene diisocyanate, dodecamethylene diisocyanate, tetradecamethylene diisocyanate, derivatives of lysine diisocyanate, tetramethylxylylene diisocyanate, 2,4,4- and/or 2,2,4-trimethylhexane diisocyanate or tetramethylhexane diisocyanate, and particularly preferred cycloaliphatic diisocyanates are 1,4-, 1,3- or 1,2-diisocyanatocyclohexane, 4,4'- or 2,4'-di(isocyanatocyclohexyl)methane, 1-isocyanato-3,3,5-trimethyl-5-(isocyanatomethyl)cyclohexane (isophorone diisocyanate), 1,3- or 1,4-bis(isocyanatomethyl)cyclohexane or 2,4-, or 2,6-diisocyanato-1-methylcyclohexane and also 3 (or 4), 8 (or 9)-bis(isocyanatomethyl)tricyclo[5.2.1.0$^{2.6}$]decane isomer mixtures. The aliphatic or cycloaliphatic isocyanates are preferably hexamethylene diisocyanate or isophorone diisocyanate, particularly preferably hexamethylene diisocyanate. It is also possible for mixtures of the diisocyanates mentioned to be present.

2,2,4- and 2,4,4-Trimethylhexamethylene 1,6-diisocyanate are usually, as a result of the method of production, obtained as an isomer mixture in a ratio of from 1.5:1 to 1:1.5, preferably 1.2:1-1:1.2, particularly preferably 1.1:1-1:1.1 and very particularly preferably 1:1.

Diisocyanates can be prepared industrially by, for example, phosgenation of diamines by the processes described in DE-C 20 05 309 and DE-A 2 404 773 or by a phosgene-free process (dissociation of urethanes) as described in EP-B-0 126 299 (U.S. Pat. No. 4,596,678), EP-B-0 126 300 (U.S. Pat. No. 4,596,679), EP-A-0 355 443 (U.S. Pat. No. 5,087,739) and in EP-A-0 568 782. According to the invention, it is immaterial whether the isocyanate used has been obtained by a phosgene-free or a phosgene-comprising production route.

Diisocyanates from the two production methods are equally preferred.

Isocyanates originating from a phosgenation process frequently have a total chlorine content of 100-800 mg/kg (determined by the Wickbold method), while the isocyanates prepared by a phosgene-free route have a total chlorine content of less than 80 mg/kg, preferably less than 60 mg/kg, particularly preferably less than 40 mg/kg, very particularly preferably less than 20 mg/kg and in particular less than 10 mg/kg.

The total bromine content (determined by the Wickbold method) is generally less than 100 mg/kg, preferably less than 50 mg/kg and especially less than 20 mg/kg.

The content of hydrolyzable chlorine is determined in accordance with ASTM D4663-98 and is less than 200 ppm, preferably less than 40 ppm, particularly preferably less than 30 ppm and very particularly preferably less than 20 ppm by weight.

The polyisocyanates comprising biuret groups are reacted by mixing with at least one, preferably precisely one, diamine b).

Typical organic diamines having exclusively aliphatically and/or cycloaliphatically bound primary and/or secondary amino groups have a molecular weight below 300. Examples are 1,2-diaminoethane, 1,2-diaminopropane, 1,3-diamino-1,1-dimethylpropane, 1,3-diamino-2,2-dimethylpropane, 1,3-diaminopropane, 1,4-diaminobutane, 1,5-diaminopentane, neopentanediamine, 1,5-diamino-2-methylpentane, 1,6-diaminohexane, 1,6-diamino-2,2,4-trimethylhexane and/or 1,6-diamino-2,4,4-trimethylhexane, 1,4- and/or 1,5-diaminohexane, 1,1-bis(aminomethyl)cyclopentane, 2,4- and/or 2,6-diamino-1-methylcyclohexane, 1-amino-3,3,5-trimethyl-5-aminomethylcyclohexane, (isophoronediamine), 1,2-bis(aminomethyl)-4-methylcyclohexane, 1,8-diaminooctane, 1,3- and/or 1,4-bis(aminomethyl)cyclohexane, 4,4'-diaminodicyclohexylmethane or 3,3'-dimethyl-4,4'-diaminodicyclohexylmethane, tetramethylxylylenediamine (TMXDA). Any mixtures of such diamines can likewise be used. 4,4'-diaminodicyclohexylmethane, isophoronediamine and 1,6-diaminohexane are particularly preferred, with very particular preference being given to isophoronediamine and 1,6-diaminohexane and in particular 1,6-diaminohexane.

Furthermore, it is also possible to use diamines of polyethers, preferably polyethylene glycols and polypropylene glycols, among which 3-oxapentane-1,5-diamine, 4,9-dioxadodecane-1,12-diamine, 4,7,10-trioxamidecane-1,13-diamine, propylene oxide derivatives such as Jeffamine® or Polyetheramine D 230, D 400, D 2000, D 4000 from Huntsman or BASF SE, polyethylene/polypropylene derivatives such as Jeffamine® EDR-176, ED-600, ED-900, ED-2003, HK-511, and also polytetrahydrofuran derivatives such as Polytetrahydrofuranamine 1700, and also polytetrahydrofuran-polypropylene glycol derivatives such as Jeffamine® THF-100, THF-140, XTJ-542, XTJ-559, are preferred. The use of mixtures is also conceivable in each case.

It is likewise possible to use triamines, for example polyethertriamines such as 3-aminomethyl-1,6-hexamethylenediamine, 4-aminomethyl-1,8-octanemethylenediamine, Polyetheramine or Jeffamine® T 403, T 3000 and T 5000 from BASF SE or Huntsman.

An advantage of direct biuretization, i.e. the direct reaction of amines with isocyanates to form biurets, is that the use of amines instead of water avoids the necessity of firstly building up the amine to isocyanate and subsequently hydrolyzing the latter by means of water back to the amine.

Furthermore, the formation of reaction gases, in particular carbon dioxide (and isobutene) as by-product of the reaction and in the offgas can be avoided by dispensing with hydrolysis.

A further advantage of direct biuretization is that the choice of amines is not restricted to the amines prescribed (via hydrolysis) by the availability of isocyanate monomers.

A further advantage of direct biuretization is that it is also not necessary to use the same basic molecular structures as in the case of the isocyanate monomers.

In carrying out the process of the invention, the abovementioned isocyanates a) and diamines b) are reacted in ratios corresponding to a ratio of equivalents of isocyanate groups to amino groups of at least 4:1, preferably from 4:1 to 50:1, particularly preferably from 5:1 to 40:1 and in particular from 5:1 to 30:1, with the primary amino groups being treated as monofunctional groups in the calculation. These data are based on the raw materials used.

The conversion of the total mass of isocyanates a) is preferably in the range from 5 to 70%, preferably from 10 to 55%, particularly preferably from 20 to 40%. The diamine b) is reacted completely in the reaction, and the excess of isocyanate a) is distilled off.

The diamine b) can be introduced in liquid or gaseous form, preferably liquid form, into the reaction.

The reaction can optionally be carried out in the presence of at least one catalyst c).

It is an advantage of the process of the invention that a catalyst can be dispensed with.

However, one possible embodiment of the present invention provides for a catalyst to be present.

In a preferred embodiment, the addition of a catalyst can be omitted at a temperature above 170° C.

In a further, preferred embodiment, the reaction can be accelerated by addition of a catalyst at a temperature of up to 190° C., in particular up to 180° C., in particular up to 170° C.

Catalysts can be, for example, OH-acid compounds as are known from DE-A144 43 885. These have the advantage that they are relatively nonvolatile and can therefore be filtered off, optionally as salts, from the product mixture or can remain as noninterfering compounds in the end product and form likewise noninterfering decomposition products or by-products during the reaction. A further advantage is the good catalytic activity of the acids.

In the process of the invention, any acids, preferably protic acids having a pKa of <10, particularly preferably <9 and very particularly preferably <8, are used as catalysts.

Possible protic acids are, for example, hydrogensulfates, in particular tetraalkylammonium hydrogensulfates whose aliphatic, branched aliphatic or araliphatic radicals have from 1 to 30, preferably from 4 to 20, carbon atoms.

Anhydrous mineral acids such as hydrogen chloride gas, sulfuric acid or oleum are also conceivable.

Further examples are sulfonic acids such as methanesulfonic acid, ethanesulfonic acid, propanesulfonic acid, 2- or 4-toluenesulfonic acid, benzenesulfonic acid, cyclododecanesulfonic acid, camphorsulfonic acid or naphthalene-1- or -2-sulfonic acid, and also monocarboxylic and dicarboxylic acids such as formic acid, acetic acid, propionic acid, butyric acid, pivalic acid, stearic acid, cyclohexanecarboxylic acid, oxalic acid, malonic acid, succinic acid, adipic acid, benzoic acid or phthalic acid.

Among these, the dicarboxylic acids mentioned are less preferred if they liberate water in significant amounts, for example more than 10 mol % of the amount used, preferably more than 8 mol %, particularly preferably more than 5 mol % and very particularly preferably more than 3 mol %, under the reaction conditions, since these can liberate water as biuretizing agent by anhydride formation.

The (ar)aliphatic carboxylic acids described, for example, in EP-A-259 233 have been found to have a relatively low effectiveness.

Acids which are preferably used and have been found to be particularly useful are: phosphoric acids and/or monoalkyl and/or dialkyl esters or monoaryl and/or diaryl esters thereof and/or hydrogensulfate. Preference is given to using monoalkyl and/or dialkyl esters or monoaryl and/or diaryl esters of phosphoric acid whose aliphatic, branched aliphatic, araliphatic or aromatic radicals have from 1 to 30, preferably from 4 to 20, carbon atoms.

Particular preference is given to using diisopropyl phosphate, di(2-ethylhexyl) phosphate, di(n-butyl)phosphate and dihexadecyl phosphate.

In a further embodiment, lower-valence acid derivatives of phosphoric acid, for example phosphorous acid, can be used.

In a further embodiment, the packing comprises catalytically active solid components such as acidic ion exchangers. These can completely or partly replace a catalyst added to the raw material stream.

These acids are used in the process of the invention in amounts of from 0.01 to 1.0% by weight, preferably from 0.02 to 0.5% by weight and very particularly preferably from 0.05 to 0.5% by weight, based on the total amount of diisocyanates used. The acids can be added as a solution or dispersion in a suitable solvent. The acids are preferably added in undiluted form.

Further catalysts which can be used are, for example, strong inorganic Lewis or Brönsted acids such as boron trifluoride, aluminum trichloride, sulfuric acid, phosphorous acid, hydrochloric acid and/or salts of nitrogen-comprising bases and inorganic and/or organic acids, as are described in DE-A-19 31 055, page 3, last paragraph to page 6, first complete paragraph, which is hereby incorporated by reference into the present disclosure.

If desired, a small amount of a stabilizer f) selected from the group consisting of urea, ammonia, biuret, urea derivatives or carboxamides as are described in WO 96/25444, preferably urea, N-methylurea, N-ethylurea, N,N-dimethylurea, N,N'-dimethylurea, N,N-diethylurea, N,N'-diethylurea, ethyleneurea or phenylurea, particularly preferably urea, can additionally be added.

The abovementioned stabilizers, for example urea, can optionally also be dissolved in water.

Such stabilizers are used in amounts of 0.01-2.0 mol %, preferably 0.05-1 mol %, based on the isocyanate groups in (a).

In a preferred embodiment, these stabilizers are dissolved or dispersed in at least one solvent d), as listed below.

To achieve better suppression of the formation of insoluble polyureas, it is possible, optionally, to make additional use of a solvent d) as solubilizer. Solvents suitable for this purpose are, for example, ethers such as dioxane or tetrahydrofuran; alkoxyalkyl carboxylates such as triethylene glycol diacetate, butyl acetate, 1-methoxypropyl 2-acetate, methyloxyethyl-2-acetate, propylene glycol diacetate; ketones such as 2-butanone, 4-methyl-2-pentanone, cyclohexanone, aromatic solvents, for example toluene, xylene, aromatic mixtures having 8-20 carbon atoms, chlorobenzene, o-dichlorobenzene, hexane, hydrocarbon mixtures, and/or trialkyl phosphates. Preference is also given to N-methylpyrrolidone and other N-(cyclo)alkylpyrrolidones such as N-methylpyrrolidone, N-ethylpyrrolidone, N-n-butylpyrrolidone and N-cyclohexylpyrrolidone.

According to the invention, preference is given to using methoxypropyl acetate, methoxyethyl acetate, trimethyl phosphate, tri-n-butyl phosphate and triethyl phosphate.

It is also possible for any mixtures of the solvents to be used.

If a solvent is used, the diamine is preferably dissolved in it and this diamine solution is introduced into the reaction. In this case, the concentration of the diamine in the solvent is from 2 to 100% by weight (solvent-free), preferably from 5 to 30% by weight, particularly preferably from 10 to 25% by weight and very particularly preferably from 15 to 20% by weight.

However, a preferred embodiment of the present invention provides for the reaction to be carried out in the absence of solvents.

The compound e) can be liquid or gaseous water or at least one water-releasing compound. The latter can be, for example, tert-butanol or dicarboxylic acids which can release water by anhydride formation, or compounds comprising water of crystallization. The addition of such compounds is less preferred.

The reaction mixture can additionally comprise inert gas streams, e.g. comprise a liquid or gaseous inert stream. The inert stream is preferably introduced in gaseous form. Possible inert media are all gases which do not react significantly, i.e. to an extent of less than 5 mol %, preferably less than 2 mol %, particularly preferably less than 1 mol %, under the reaction conditions, with the isocyanate stream, the amine-comprising stream and/or the catalyst. Examples are CO, $N_2$, He, Ar, hydrocarbons such as methane, etc., and mixtures thereof. Preference is given to using argon and/or nitrogen. Particular preference is given to using nitrogen.

According to the invention rotating fixed-bed reactors are used as mixing device in step i).

For the purposes of the invention, a rotating fixed-bed reactor (also known as rotating packed bed or hi-gee reactor) is understood to mean a reactor in which a liquid phase impinges on a rotating solid element with a difference in the relative velocity, which leads to dispersion and mixing of the liquid phase.

Preferred rotating fixed-bed reactors can have structured or unstructured packing as rotating solid element by means of which mixing of the liquid phase occurs.

In a preferred form, the reactor comprises a continuous gas phase. Here, high film and droplet flow occurs on the packing. For the present purposes, film flow is a three-phase system of packing, liquid and gas phase. Droplet flow is a two-phase liquid-gas system when, after initial mixing of polyisocyanate and diamine component, the mixture thereof flies out from the outer edges of the packing. The presence of a gas phase allows film formation and three-phase formation. The gas phase has to be present in at least such an amount that a continuous gas phase is present within the packing.

FIG. 1 shows an illustrative schematic embodiment of a rotating fixed-bed reactor as can be used for the present invention.

The reference numerals therein are as follows:
1 Introduction of liquid ((cyclo)aliphatic diisocyanate and/or polyisocyanate a) and (cyclo)aliphatic diamine b)
2 Packing/rotor
3 Housing
4 Gas outlet (via hollow shaft)
5 Liquid outlet
6 Drive shaft
7 Gas inlet (e.g. for inert gas)
$R_1$: Housing radius
$R_2$: External radius between axis of rotation and packing, thickness of the mixing zone
$R_3$: Internal radius between axis of rotation and packing
$H_1$: Height of housing
$H_2$: Height of packing As elements 2, mention may here be made of, for example, structured internals such as packings (including packings made of wire meshes and woven fabrics), static mixers, metal dividing sheets, metal plates (thin, corrugated and/or perforated) and also unstructured porous systems such as beds or packing elements or open-pored foam structures.

(Cyclo)aliphatic diisocyanate and/or polyisocyanate a) and (cyclo)aliphatic diamine b) are introduced separately. They can, for example, be fed in via a plurality of separate nozzles or lances.

After introduction of (cyclo)aliphatic diisocyanate and/or polyisocyanate and (cyclo)aliphatic diamine, the liquid stream moves from the middle outward over the packing and then flows in mixed and at least partially reacted form out of the mixing device via the liquid outlet.

According to the invention, the acceleration acting on the liquid phase in the mixing device is at least 100 g, preferably 100-2000 g, particularly preferably 500-1000 g. The high acceleration reduces buildup effects of the liquid in the countercurrent. Throughput and space-time yield can be increased in this way.

The velocity of the liquid phase in the mixing device is generally 0.001-1 m/s, preferably 0.003-0.05 m/s.

The addition of inert gases is necessary to ensure the presence of a gas phase in the rotating fixed-bed reactor so that the packing is not flooded and good mixing is thus ensured.

In the embodiment depicted in FIG. 1, the gas stream is introduced via the housing, flows through the packing in countercurrent to the stream of liquid and exits again via the hollow shaft.

The liquid is generally introduced at temperatures of at least 30° C. above the melting point of the amines; in the case of hexamethylenediamine, preferably above 60° C., in particular above 80° C.

Mixing preferably takes place at an exit temperature from the rotating fixed-bed reactor i) at above 120° C., in particular above 140° C. The upper limit to the temperature is preferably selected so that it is not higher at the liquid outlet from i) than that in the subsequent reaction reactor ii). Here, the heat evolved in the reaction of (cyclo)aliphatic diisocyanate and/or polyisocyanate (a) and (cyclo)aliphatic diamine (b) in the rotating fixed-bed reactor has to be taken into account.

The upper limit to the temperature of the reaction mixture during the mixing step i) is less than 270° C., preferably not more than 250° C., very preferably not more than 200° C.

The absolute pressure at the outlet of the mixing device is in the range from 0.3 bar to 10 bar, preferably from 0.6 bar to 7 bar, particularly preferably from 0.8 bar to 5 bar.

In the mixing device, the starting materials a) and b) and the catalyst c) are mixed with or without solvent and with or without inert gas and with or without compound e).

As reaction apparatuses for step ii), it is possible to use all customary residence reactors, e.g. stirred vessels, jet loop reactors, tube reactors, vessels, columns. Combinations or multiple use of the apparatus types are also possible. For example, a stirred vessel can be combined with a tube reactor. A cascade of stirred vessels can also be used as reaction apparatus in the process.

When the reaction apparatus is made up of one or more stirred vessels, the flow state is preferably set so that the Newton number which characterizes the power input is not inversely proportional to the Reynolds number formed by the stirrer diameter when the rotational speed is varied. The flow state is particularly preferably set so that the Newton number is not a function of the Reynolds number when the rotational speed is varied.

When the reactor is a tube reactor without internals, the Reynolds number is preferably at least 2300, particularly preferably at least 2700, very particularly preferably at least 3000, in particular at least 4000, at least 7000 or especially at least 10 000.

Preference is given to using at least one stirred vessel through which longitudinal flow occurs and which has a diameter to length ratio of from 1:1.2 to 1:10, preferably from 1:1.5 to 1:6.

The power input per unit volume in this stirred vessel should be at least 0.1 watt/l, preferably at least 0.3 watt/l, particularly preferably at least 0.5 watt/l. In general, up to 20 watt/l, preferably up to 6 watt/l and particularly preferably up to 2 watt/l, are sufficient.

The power can be introduced via all possible types of stirrer, e.g. inclined blade stirrers, anchor stirrers, disk stirrers, turbine stirrers, beam stirrers. Preference is given to using disk stirrers and turbine stirrers.

It is also possible for a plurality of stirrers to be installed on the shaft. Preference is given to using one stirrer on the shaft per segment of the cascade. The diameter of the stirring elements is from 0.1 to 0.9 times the diameter of the stirred vessel, preferably from 0.2 to 0.6 times the diameter of the stirred vessel.

The stirred vessel or cascaded stirred vessel can be operated with or without baffles. It is preferably operated using baffles. It is usually operated using from 1 to 10 baffles, preferably from 2 to 4 baffles, per segment.

After leaving the mixing stage i), the reaction mixture is fed to the reaction apparatus. If an inert gas is present, the reaction apparatus can, in a preferred embodiment, be a predominantly vertical apparatus (for example a vertical tube reactor, column or slim stirred vessel). In this case, the reaction mixture can be fed in from the bottom (cocurrent flow of the liquid phase with the inert gas) or from the top (flow in countercurrent to the inert gas), preferably from below.

Any inert gas fed in can be taken off at any point in the system. It is preferably taken off only after the reaction mixture has reacted completely.

The residence time in the reaction apparatus ii) is preferably in the range from 1 min to 8 hours, preferably from 1 min to 8 hours, particularly preferably from 30 min to 6 hours and very particularly preferably from 1 to 4 hours. The reaction time is advantageously selected so that the theoretical NCO value is reached at the end. The theoretical NCO value is the NCO value which the reaction mixture has when all of the amine used has formed the amount of biuret groups to be theoretically expected.

The temperature in the region of the reaction section ii) is in the range from 30 to 300° C., preferably from 80 to less than 300° C., particularly preferably from 120 to 250° C.

The absolute pressure in the reaction apparatus is in the range from 0.3 to 100 bar, preferably from 0.5 to 10 bar, particularly preferably from 0.6 to 4 bar, particularly preferably from 0.8 to 2 bar.

The catalyst c) is added to the reaction mixture in the mixing device i). Instead of this or in addition, the mixing-in of the catalyst stream can occur separately in the reaction apparatus ii) or at a plurality of points. The catalyst is preferably mixed into one of the streams which are fed to the rotating fixed-bed reactor. The catalyst stream is particularly preferably introduced into the stream comprising isocyanate groups which goes into the mixing device.

In the simplest embodiment, the invention comprises the combination mixing device i) and reaction apparatus ii). Here, the isocyanate stream a) and catalyst c) are then premixed and mixed with the amine-comprising stream b) and then introduced into the reaction apparatus ii) after passing through the mixing device. The mixing device i) and the reaction apparatus ii) do not in this case have to be separate apparatuses but instead the reaction apparatus ii) can also directly adjoin the mixing device.

In the mixing device i), the reaction can commence immediately after mixing of the components, so that the reaction is not necessarily restricted to the reaction apparatus ii).

(Cyclo)aliphatic di- and/or polyisocyanate and catalyst are continuously fed into the mixing device and the mixture of amine and optionally solvent is introduced in parallel thereto. The crude product comprising biuret oligomers and excess monomers is discharged continuously. The reaction apparatus ii) can be operated batchwise or continuously, preferably continuously. The crude product is subsequently worked up by means of distillation.

In general, it will be necessary to obtain products which do not liberate dangerous amounts of isocyanates during work-up to separate the major part of the unreacted isocyanates (a) from the polyisocyanates comprising biuret groups formed. It is usually desirable to obtain products whose content of monomeric isocyanates (a) is less than 1% by weight, preferably less than 0.5% by weight, particularly preferably less than 0.3% by weight and very particularly preferably less than 0.2% by weight, based on the polyisocyanates comprising biuret groups. The excess diisocyanates from (a) are advantageously separated off under reduced pressure at temperatures which are in the range from 50° C. to the reaction temperature selected in the reaction by, for example, distilling them off.

Apparatuses used for this purpose are flash evaporators, falling film evaporators, thin film evaporators or short path evaporators which can optionally be superposed by a distillation column.

The distillation is generally carried out at a pressure in the range from 0.1 to 300 hPa, preferably below 200 hPa and particularly preferably below 100 hPa.

The unreacted diisocyanate a) which has been separated off and recovered in this way can advantageously be reused in the reaction.

If a solvent has been used in the reaction, this is likewise preferably separated off from the reaction mixture by distillation. The distillation conditions and apparatuses are, for instance, the same as in the removal of the excess diisocyanate.

Figure 2:
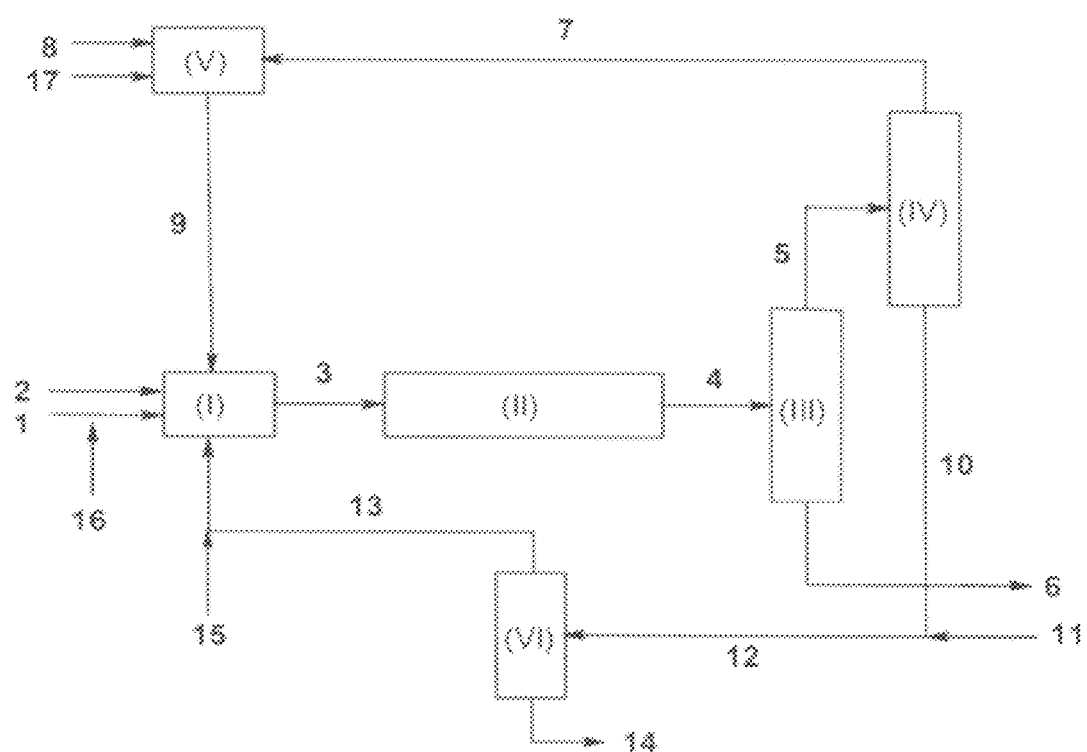
FIG. 2 shows a schematic view of a process of one embodiment of the invention.

The present invention further provides a process for preparing polyisocyanates comprising biuret groups by reacting a diisocyanate with a diamine in the presence of at least one acid and optionally a solvent, which comprises mixing the (cyclo)aliphatic di- and/or polyisocyanate stream 1 and the diamine stream 2 and also a stream 9 of recirculated solvent, if one is present, and recirculated excess diisocyanate 13 with one another in the presence of at least one catalyst in a mixing device (I), then feeding the resulting mixture of diamine and diisocyanate into at least one reaction apparatus (II) and reacting it to form the polyisocyanate comprising biuret groups, subsequently separating any solvent present, excess diisocyanate and polyisocyanate comprising biuret groups from one another by distillation and recirculating any solvent present and the excess diisocyanate to the mixing device (I) (cf. FIG. 2).

The streams of (cyclo)aliphatic diisocyanate and/or polyisocyanate 1 and 13 are preferably mixed and fed together to the rotating fixed-bed reactor.

The process of the invention can, in one embodiment, be carried out in the presence of a solvent, as shown in FIG. 2:

The process comprises, in one possible embodiment, a mixing device (I), at least one reaction apparatus (II), two distillation apparatuses (III) and (IV) and optionally a further mixing device (V) and optionally a further distillation unit (VI). The distillation units (III) to (VI) can also be replaced by any other arrangements of distillation units in a different number and design as long as a product having a sufficient purity is obtained.

Diisocyanate and/or polyisocyanate stream 1 and diamine stream 2 and also a stream 9 of solvent and recirculated excess diisocyanate 13, where the streams 1 and/or 13 have optionally been admixed with catalyst 15, are mixed with one another in the mixing device (I), according to the invention a rotating fixed-bed reactor. In this case, the fresh stream 8 of solvent can be significantly reduced or possibly set to zero.

Preference is given to the diamine as stream 17 instead of stream 2 being mixed with recirculated solvent 7 in an upstream mixing unit (V) and this mixture being fed as stream 9 into the mixing unit (I). In this case the stream 2 is zero.

The mixture of diamine and diisocyanate and/or polyisocyanate obtained in the mixing unit (I) is then fed into at least one reaction apparatus (II) and reacted to form the polyisocyanate comprising biuret groups.

The resulting reaction mixture 4 is then fed into the first distillation unit (III) in which the excess diisocyanate and solvent are separated off together as low boiler stream 5.

The distillation unit (III) can have one or more theoretical plates; preference is given to a multistage, preferably at least two-stage, particularly preferably at least three-stage, very particularly preferably at least four-stage, cascade of flash evaporators, falling film evaporators, thin film evaporators and/or short path evaporators.

The outflow 6 from the distillation unit (III) is the polyisocyanate comprising biuret groups as desired product, which can generally be processed further without further purification.

The vapor from the distillation unit (III), which comprises excess diisocyanate and solvent, is then fed into a further distillation unit (IV) in which the solvent, which preferably has a boiling point lower than that of the diisocyanate, is separated off as gaseous low-boiler stream 7 from the excess diisocyanate as bottoms 10.

The distillation unit (IV) is, for example, a distillation unit having from 5 to 40, preferably from 10 to 30, theoretical plates.

To remove relatively high molecular weight impurities comprised in the excess diisocyanate from the bottoms 10, this stream can optionally be subjected to a preferably multistage evaporation (VI), for example in a falling film evaporator. The purified diisocyanate 13 taken off at the top is then optionally admixed with catalyst 15 and fed to the mixing unit (I), while the bottoms 14 are discarded.

In a preferred embodiment when the distillation unit (VI) is present, the fresh diisocyanate and/or polyisocyanate is not fed directly via stream 1 to the mixing unit but is instead mixed as stream 11 into stream 10 and this mixture 12 is then distilled. This distillation of the fresh diisocyanate feed generally achieves a further improvement in the quality, in particular the color quality, of the product.

Figure 3:
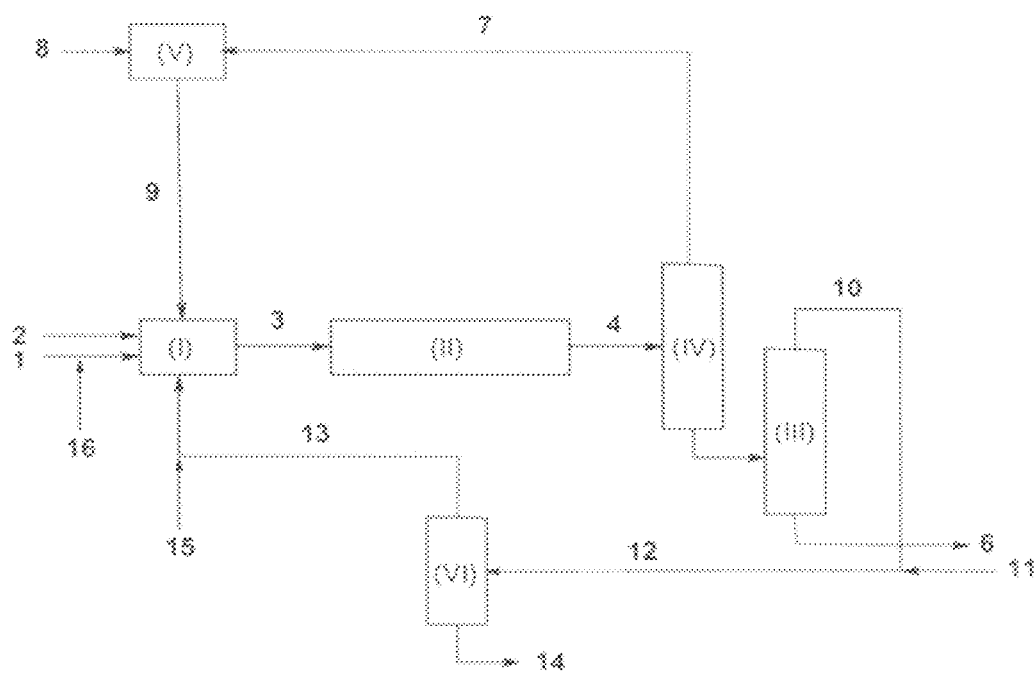
FIG. 3 shows a schematic view of a process of another embodiment of the invention.

A further preferred embodiment is shown in FIG. 3 and differs from that shown in FIG. 2 in the arrangement of the distillation units (III) and (IV):

In this embodiment, the reaction mixture 4 obtained from the reaction apparatus (II) is firstly fed to a distillation unit (IV) which preferably has from 5 to 40, particularly preferably from 10 to 30, theoretical plates, the solvent 7 is separated off as low boiler and the stream 15 comprising excess diisocyanate and polyisocyanate comprising biuret groups is taken off at the bottom and preferably fed to the distillation unit (III) which is a multistage, preferably at least two-stage, particularly preferably at least three-stage, very particularly preferably at least four-stage, cascade of flash evaporators, falling film evaporators, thin film evaporators and/or short path evaporators.

There, the excess diisocyanate is taken off as vapor 10 and recirculated as described above and the polyisocyanate comprising biuret groups 6 is taken off as bottoms.

In a preferred embodiment, the recycle stream of isocyanate and the fresh (cyclo)aliphatic diisocyanate feed are combined.

In a preferred simplified embodiment, the distillation apparatus IV in FIG. 2 can be omitted and the distillate stream 5 can be introduced without separation of (cyclo)aliphatic diisocyanate and solvent into the rotating fixed-bed reactor or the stream of (cyclo)aliphatic diisocyanate and/or polyisocyanate 1.

In a preferred embodiment, the solvent streams are introduced into stream 1 of (cyclo)aliphatic diisocyanate and/or polyisocyanate and/or stream 2 of (cyclo)aliphatic diamine and/or stream 15 (catalyst).

In a preferred embodiment, no solvent is used, diisocyanate is separated from the biuret in a distillation apparatus (III), mixed with fresh diisocyanate and/or polyisocyanate, catalyst is optionally added and this stream is introduced separately from the diamine stream into the rotating fixed-bed reactor.

The optional catalyst is preferably added to the diisocyanate and/or polyisocyanate stream and not separately.

In a further embodiment, the catalyst is added only downstream of the rotating fixed-bed reactor and upstream of the reaction apparatus.

The process described according to the invention generally gives clear products having a color number of less than 100, preferably less than 50, particularly preferably less than 20 APHA in accordance with DIN ISO 6271 and/or a viscosity of from 1000 to 15 000 mPas, preferably from 1000 to 10 000 mPas at 23° C. in accordance with DIN 53019 Part 1 (rotational viscometer).

The surface coatings industry requires, in particular, polyisocyanates comprising biuret groups which have a viscosity of from 2000 to 15 000 mPas, preferably from 2500 to 10 000 mPas (based on a solids content of 100% and measured at a temperature of 23° C. and a shear rate of 100 s$^{-1}$). Such polyisocyanates can, if necessary, be diluted with solvents, for example the abovementioned solvents, preferably ethyl acetate, butyl acetate, methoxypropyl acetate, xylene and aromatic mixtures having 8-20 carbon atoms and mixtures thereof.

Apart from polyisocyanates comprising biuret groups, lesser amounts of polyisocyanates comprising uretdione and/or carbodiimide groups and/or isocyanurate, and also, in the presence of alcohols, polyisocyanates comprising allophanate groups can also be comprised.

Since the process of the invention is carried out in the absence of water or water-releasing compounds, no carbon dioxide ($CO_2$), which partly dissolves in the reaction mixture and/or can partly form a gas phase in addition to the reaction mixture, is formed in the process of the invention.

Due to the absence of carbon dioxide in the reaction mixture, no polyisocyanates comprising oxadiazinetrione groups are formed. In general, the proportion of polyisocyanates comprising oxadiazinetrione groups in the reaction mixture according to the invention is less than 1% by weight, preferably 0.75% by weight, particularly preferably less than 0.5% by weight, very particularly preferably less than 0.3% by weight and in particular less than 0.1% by weight.

The polyisocyanates comprising biuret groups which are obtained by the process of the invention can also subsequently be reversibly blocked by means of blocking groups.

The polyisocyanates comprising biuret groups which are obtained by the process of the invention are generally used in the surface coatings industry and can, for example, be used in coating compositions for one-component or two-component polyurethane coatings, for example for primers, primer-surfacers, basecoats, unpigmented topcoats, pigmented topcoats and clear varnishes in the field of industrial surface coating, in particular surface coating for aircraft, ships or large vehicles, surface coating of wind power plants, surface coating of wood or plastics, surface coating of automobiles, in particular OEM coating or automobile repair coating, or decorative surface coating. The coating compositions are particularly suitable for applications in which a particularly high application reliability, exterior weathering resistance, optics, solvent resistance and/or resistance to chemicals are required. The curing of these coating compositions is not significant for the purposes of the invention. In the automobile industry in particular, multilayer cures, e.g. of clear topcoat and basecoat (known as two-in-one) or of primer-surfacer, clear topcoat and basecoat (known as three-in-one), are increasingly being carried out.

REFERENCE SYMBOLS IN FIG. 1

1 Introduction of liquid ((cyclo)aliphatic diisocyanate and/or polyisocyanate a) and (cyclo)aliphatic diamine b)
2 Packing/rotor
3 Housing
4 Gas outlet (via hollow shaft)
5 Liquid outlet
6 Drive shaft
7 Gas inlet (e.g. for inert gas)
$R_1$: Housing radius
$R_2$: External radius between axis of rotation and packing, thickness of the mixing zone
$R_3$: Internal radius between axis of rotation and packing
$H_1$: Height of housing
$H_2$: Height of packing

REFERENCE SYMBOLS IN FIGS. 2 AND 3

1: Introduction of liquid (cyclo)aliphatic diisocyanate and/or polyisocyanate
2: Introduction of liquid (cyclo)aliphatic diamine
3: Reaction mixture of (cyclo)aliphatic diisocyanate and/or polyisocyanate and (cyclo)aliphatic diamine between rotating fixed-bed reactor and reaction apparatus
4: Reaction mixture of (cyclo)aliphatic diisocyanate and/or polyisocyanate and (cyclo)aliphatic diamine downstream of the reaction apparatus
5: Distillate composed of (cyclo)aliphatic diisocyanate and solvent
6: Biuret-comprising polyisocyanate
7: Recirculated solvent (optional)
8: Fresh solvent (optional)
9: Introduction of liquid solvent (optional)
10: (Cyclo)aliphatic diisocyanate from separation of (cyclo)aliphatic diisocyanate and solvent
11: Fresh (cyclo)aliphatic diisocyanate and/or polyisocyanate
12: Redistilled (cyclo)aliphatic diisocyanate or mixture of fresh (cyclo)aliphatic diisocyanate and/or polyisocyanate and (cyclo)aliphatic diisocyanate from separation of (cyclo)aliphatic diisocyanate and solvent
13: Recirculated (cyclo)aliphatic diisocyanate
14: Distillation residue separated off in the distillation of diisocyanate
15: Catalyst (optional)
16: Catalyst (optional)
17: (Cyclo)aliphatic diamine
(I): Rotating fixed-bed reactor
(II): Reaction apparatus
(III): Distillation apparatus for the separation of (cyclo)aliphatic diisocyanate (optionally solvent) and biuret-comprising polyisocyanate 6
(IV): Distillation apparatus
(V): Mixing device for solvent
(VI): Distillation apparatus

The invention claimed is:

1. A process for preparing polyisocyanates comprising biuret groups from
   a) at least one (cyclo)aliphatic diisocyanate and/or polyisocyanate,
   b) at least one (cyclo)aliphatic diamine having two primary and/or secondary amino groups,
   c) optionally at least one acid, and
   d) optionally at least one solvent,
   e) optionally in the presence of water or at least one water-releasing compound, the process comprises:
     i) mixing the components a), b) and optionally c) and also optionally d) and/or e) in a mixing device, thereby forming a reaction mixture, and ii) feeding the reaction mixture obtained in i) into at least one reaction apparatus in which the reaction mixture is treated thermally, wherein the mixing device is at least one rotating fixed-bed reactor in the absence of a stator in the region of the mixture, having an acceleration acting on the liquid phase in the mixing device of at least 100 g.

2. The process according to claim 1, wherein the (cyclo) aliphatic diisocyanate and/or polyisocyanate is selected from the group consisting of tetramethylene diisocyanate, hexamethylene diisocyanate (1,6-diisocyanatohexane), octamethylene diisocyanate, decamethylene diisocyanate, dodecamethylene diisocyanate, tetradecamethylene diisocyanate, derivatives of lysine diisocyanate, tetramethylxylylene diisocyanate, 2,4,4- and/or 2,2,4-trimethylhexane diisocyanate, tetramethylhexane diisocyanate, 1,4-, 1,3- or 1,2-diisocyanatocyclohexane, 4,4'- or 2,4'-di(isocyanatocyclohexyl)methane, 1-isocyanato-3,3,5-trimethyl-5-(isocyanatomethyl)cyclohexane (isophorone diisocyanate), 1,3- or 1,4-bis(isocyanatomethyl)cyclohexane and 2,4- or 2,6-diisocyanato-1-methylcyclohexane and mixtures thereof, in particular hexamethylene diisocyanate (1,6-diisocyanatohexane) and isophorone diisocyanate.

3. The process according to claim 1, wherein the (cyclo) aliphatic diamine is selected from the group consisting of 1,2-diaminoethane, 1,2-diaminopropane, 1,3-diaminopropane, 1,3-diamino-1,1-dimethylpropane, 1,3-diamino-2,2-dimethylpropane, 1,4-diaminobutane, 1,5-diaminopentane, neopentanediamine, 1,5-diamino-2-methylpentane, 1,6-diaminohexane, 1,6-diamino-2,2,4-trimethylhexane and/or 1,6-diamino-2,4,4-trimethylhexane, 1,4- and/or 1,5-diaminohexane, 1,1-bis(aminomethyl)-cyclopentane, 2,4- and/or 2,6-diamino-1-methylcyclohexane, 1-amino-3,3,5-trimethyl-5-aminomethylcyclohexane (isophoronediamine), 1,2-bis(aminomethyl)-4-methylcyclohexane, 1,8-diaminooctane, 1,3- and/or 1,4-bis(aminomethyl)cyclohexane, 4,4'-diaminodicyclohexylmethane, 3,3'-dimethyl-4,4'-diaminodicyclohexylmethane, tetramethylxylylenediamine (TMXDA), mixtures thereof and in particular 1,6-diaminohexane and isophoronediamine.

4. The process according to claim 1, wherein the component a) is hexamethylene diisocyanate (1,6-diisocyanatohexane) and the component b) is 1,6-diaminohexane or the component a) is isophorone diisocyanate and the component b) is isophoronediamine or the component a) is hexamethylene diisocyanate and the component b) is isophoronediamine or a cycloaliphatic diamine.

5. The process according to claim 1, wherein the components a) and b) are formally based on different amines.

6. The process according to claim 1, wherein a ratio of equivalents of isocyanate groups to amino groups in the reaction is at least 4:1.

7. The process according to claim 1, wherein the at least one acid c), which is a catalyst, is present and is a protic acid having a pKa of <10.

8. The process according to claim 7, wherein the at least one acid c) is diisopropyl phosphate, di(2-ethylhexyl) phosphate di(n-butyl) phosphate, dihexadecyl phosphate, or a mixture thereof.

9. The process according to claim 7, wherein the at least one acid is introduced into the isocyanate stream.

10. The process according to claim 1, wherein the residence time in the reaction apparatus ii) is from 15 min to 8 hours.

11. The process according to claim 1, wherein the at least one solvent d) is present.

12. The process according to claim 9, wherein the at least one solvent d) is selected from the group consisting of ethers, preferably dioxane, tetrahydrofuran; alkoxyalkyl carboxylates, preferably triethylene glycol diacetate, ethyl acetate, butyl acetate, 1-methoxypropyl 2-acetate, methoxyethyl 2-acetate, propylene glycol diacetate; ketones, preferably 2-butanone, 4-methyl-2-pentanone, cyclohexanone, hexane, toluene, xylene, aromatic mixtures having 8-20 carbon atoms, chlorobenzene, o-dichlorobenzene, trialkyl phosphates and N-(cyclo)alkylpyrrolidones.

13. The process according to claim 1, wherein a gas phase is present in the rotating fixed-bed reactor.

14. The process according to claim 1, wherein the reaction mixture additionally comprises an inert gas.

* * * * *